United States Patent [19]
Hermes et al.

[11] Patent Number: 5,734,323
[45] Date of Patent: Mar. 31, 1998

[54] PUNCTURE DETECTING BARRIER MATERIALS

[75] Inventors: Robert E. Hermes, Los Alamos, N. Mex.; David R. Ramsey, Bothel, Wash.; Joseph F. Stampfer; John M. Macdonald, both of Santa Fe, N. Mex.

[73] Assignee: The Regents of the University of California, Oakland, Calif.

[21] Appl. No.: 653,959

[22] Filed: May 28, 1996

Related U.S. Application Data

[63] Continuation-in-part of Ser. No. 418,060, Apr. 6, 1995, abandoned.

[51] Int. Cl.$^6$ .................................. G08B 21/00
[52] U.S. Cl. ............................ 340/540; 128/917
[58] Field of Search .................... 340/540, 550, 340/605; 73/40; 324/557; 128/917, 918; 604/34; 250/516.1

[56] References Cited

U.S. PATENT DOCUMENTS

| | | | |
|---|---|---|---|
| 3,025,403 | 3/1962 | Belknap et al. | 250/516.1 |
| 4,593,275 | 6/1986 | Kazandjoglou | 340/604 |
| 4,826,730 | 5/1989 | McClure | 428/421 |
| 4,884,061 | 11/1989 | Genevois | 340/550 |
| 4,909,069 | 3/1990 | Albin et al. | 73/40 |
| 4,956,635 | 9/1990 | Langdon | 340/540 |
| 5,036,309 | 7/1991 | Dennison | 340/540 |
| 5,063,370 | 11/1991 | Smith | 340/540 |
| 5,109,215 | 4/1992 | Dennison | 340/540 |
| 5,114,425 | 5/1992 | Williams et al. | 606/34 |
| 5,157,379 | 10/1992 | Dennison | 340/540 |
| 5,165,114 | 11/1992 | Dams et al. | 2/168 |
| 5,204,632 | 4/1993 | Leach | 324/557 |
| 5,289,785 | 3/1994 | Mac Pherson et al. | 109/42 |
| 5,310,517 | 5/1994 | Dams et al. | 264/255 |

OTHER PUBLICATIONS

Stampfer, Joseph F., Salazar, Johnny A., Andres, Guadalupe Trujillo, and Harris, Tammy, "Examination of Several Instruments for the Electrical Detection of Holes in Latex Gloves During Use," *Journal of Clinical Engineering*, vol. 21, No. 3, May/Jun., 1996.

Stampfer, Joseph F., Kissane, Richard J., and Martin, Linda Spencer, "Electrical Conductivity as a Test for the Integrity of Latex Gloves," *Journal of Clinical Engineering*, vol. 19, No. 6, Nov./Dec. 1994.

*Primary Examiner*—Thomas Mullen
*Attorney, Agent, or Firm*—Gemma Morrison Bennett; William A. Eklund

[57] ABSTRACT

A method and apparatus for continuous real-time monitoring of the integrity of protective barrier materials, particularly protective barriers against toxic, radioactive and biologically hazardous materials has been developed. Conductivity, resistivity or capacitance between conductive layers in the multilayer protective materials is measured by using leads connected to electrically conductive layers in the protective barrier material. The measured conductivity, resistivity or capacitance significantly changes upon a physical breach of the protective barrier material.

14 Claims, 3 Drawing Sheets

5,734,323

1

PUNCTURE DETECTING BARRIER MATERIALS

Continuation-in-Part of patent application Ser. No. 08/418,060 filed Apr. 6, 1995, now abandoned.

This invention was made with Government support under Contract No. W-7405-ENG-36 awarded by the U.S. Department of Energy. The Government has certain rights in the invention.

TECHNICAL FIELD

The present invention relates to protective barrier materials used for handling or containing hazardous materials. More particularly, the invention relates to barrier materials which are designed to perform continuous, real-time monitoring for punctures, cuts or tears in the protective barrier.

BACKGROUND ART

With the increase in hazardous materials of all sorts in private industry and government activity there is an increasing need for protective barrier materials to be used to protect workers and the public from the hazardous materials. Hazardous materials, including bioactive materials and radioactive materials, used in research and development and industrial applications, are treated and stored in various manners. During all of these phases, protective barriers of various sorts are used to separate the hazardous materials from people and equipment with which people may come into contact. Currently these protective barrier materials are tested intermittently by using such techniques as differential pressure monitoring, conductivity measurements using a liquid medium, or the use of a high voltage discharge across the barrier material. These methods cannot be used while the barrier material is in use; thus there is a need for some means of continuously monitoring the integrity of the protective barrier materials and of testing protective barrier materials while they are in use.

One very specific example of a particular need for protective barrier materials is the need for protective barrier materials to be used in making glove box gloves. Glove boxes are widely used in the handling of toxic, radioactive and biologically hazardous materials. Typical glove boxes utilize arm-length elastomeric gloves, which are affixed at their open ends to circular openings in the glove box and which can extend inwardly into the enclosure of the glove box. A user extends his or her arms into the gloves, through the openings of the glove box, so that the user can safely handle articles inside the glove box with the gloves.

Glove boxes typically have windows that enable the user to view the interior of the glove box while working with the gloves. Although for some applications a positive pressure of inert gases is maintained in glove boxes, glove boxes are generally negatively pressurized so that dust or vapors within the glove box are contained in the event of a leak, and also during changing of the gloves.

The gloves, being of flexible or elastomeric polymeric materials, are subject to wear and aging, and must typically be replaced on a regular schedule to prevent the development of leaks due to normal wear and tear, aging, and eventual cracking of the polymeric material. It is well recognized that, because the gloves are formed of flexible or elastomeric polymeric materials that are relatively easily damaged, the integrity of the gloves must be ensured to prevent exposure of the users to the hazardous materials inside the box. Present methods for detecting punctures, tears and cuts in gloves are a combination of periodic visual inspections of the gloves and intermittent testing of both the gloves and the workers. These methods, coupled with regularly scheduled replacement of the gloves, are used to ensure the integrity of the gloves. Personal inspections which use counting assays for radioactivity at the end of each work session may prevent exposure of subsequent workers, but may be too late for reducing exposure of the worker whose work session has just ended. Other simple intermittent testing techniques include pressurizing a glove with gas, or filling a glove with water, and inspecting for leaks. Such techniques are however not easily applied to gloves already installed in glove boxes, and in any event do not detect holes smaller than a few tens of microns.

Other previously known testing techniques rely on measuring the electrical conductivity between the inner and outer surfaces of a glove, most commonly by measuring the conductivity between saline solutions located inside and outside the glove. Some of these monitoring systems measure the decrease in electrical resistance caused by hydration of the glove material. While effective, these techniques are not readily applied to the gloves installed in glove boxes, and especially not while the gloves are in use.

These approaches are adequate for many purposes, depending on the nature of the materials being handled and the type of activities being performed. However, they cannot ensure against exposure accompanying a sudden failure of glove box gloves. In particular, these methods cannot ensure against exposure occasioned by small, unnoticed failures of the gloves, for example punctures, small tears or cuts caused by a sliver of wood, glass or metal. In the case of particularly toxic, radioactive or otherwise hazardous materials, such failures can result in significant adverse exposures to glove box users.

Accordingly, it is the object of the present invention to provide puncture detecting protective barrier materials.

It is another object of the present invention to provide puncture detecting protective barrier materials which enable continuous real-time monitoring for failure of the integrity of the protective barrier.

It is more specifically another object of the present invention to provide puncture detecting protective barrier materials which are useful for separating toxic, bioactive, radioactive, or otherwise hazardous materials from people and equipment with which people may come into contact.

It is also an object of the present invention to provide an improved glove box glove that enables prompt detection of a failure of the barrier integrity of the glove.

It is yet another object of the present invention to provide a glove box glove that enables continuous real-time monitoring for detection of even small failures of the barrier integrity of a glove box glove.

It is a further object of the present invention to provide a method of detecting breaches of the integrity of a protective barrier material.

DISCLOSURE OF INVENTION

The foregoing objectives are attained by the invention of multilayer materials comprising external layers, at least one internal layer of an electrically insulating material, and first and second electrically conductive layers, the first and second electrically conductive layers being located on opposite sides of an internal layer of electrically insulating material, and with a means for measuring conductivity connected to each of the first and second electrically conductive layers. The first and second electrically conductive layers can be the same as the external layers or can be separate layers.

Breaches of the integrity of a protective barrier material can be detected by measuring the electrical conductivity between two electrically conductive layers separated by an electrically insulative layer in the barrier material.

Suitable electrical signal measuring devices may be used to measure the resistance, conductivity or capacitance between the two conductive layers to thereby produce a real-time indication of a puncture, cut or tear of the material. When any puncture, cut or tear occurs in the protective barrier material, normal conductivity and capacitance across the electrically insulative layer in the protective barrier material is altered. Leads in electrical contact with the electrically conductive layers in the protective barrier material can enable continuous, real-time measurement, monitoring and other recordation of the alteration in the resistance, conductivity or capacitance indicative of a breach in the integrity of the protective barrier material.

This protective barrier material and method is particularly suited for any applications requiring the separation of toxic, bioactive, radioactive mad other hazardous materials from people and equipment with which people may come into contact. The protective barrier material and method of this invention are useful for containment bags, container liners, environmental liners, covers for hazardous storage containers, gaskets or seals and protective apparel such as gloves, aprons, boots, pants, smocks, face shields, gowns and the like.

The present invention is particularly appropriate for manufacture of gloves for use in glove boxes, and is even more particularly suited to gloves used for handling radioactive materials, where prompt detection of punctures, cuts or tears is desirable to avoid prolonged exposure to and dispersal of radioactive contaminants.

BEST MODES FOR CARRYING OUT THE INVENTION

Figure 1:
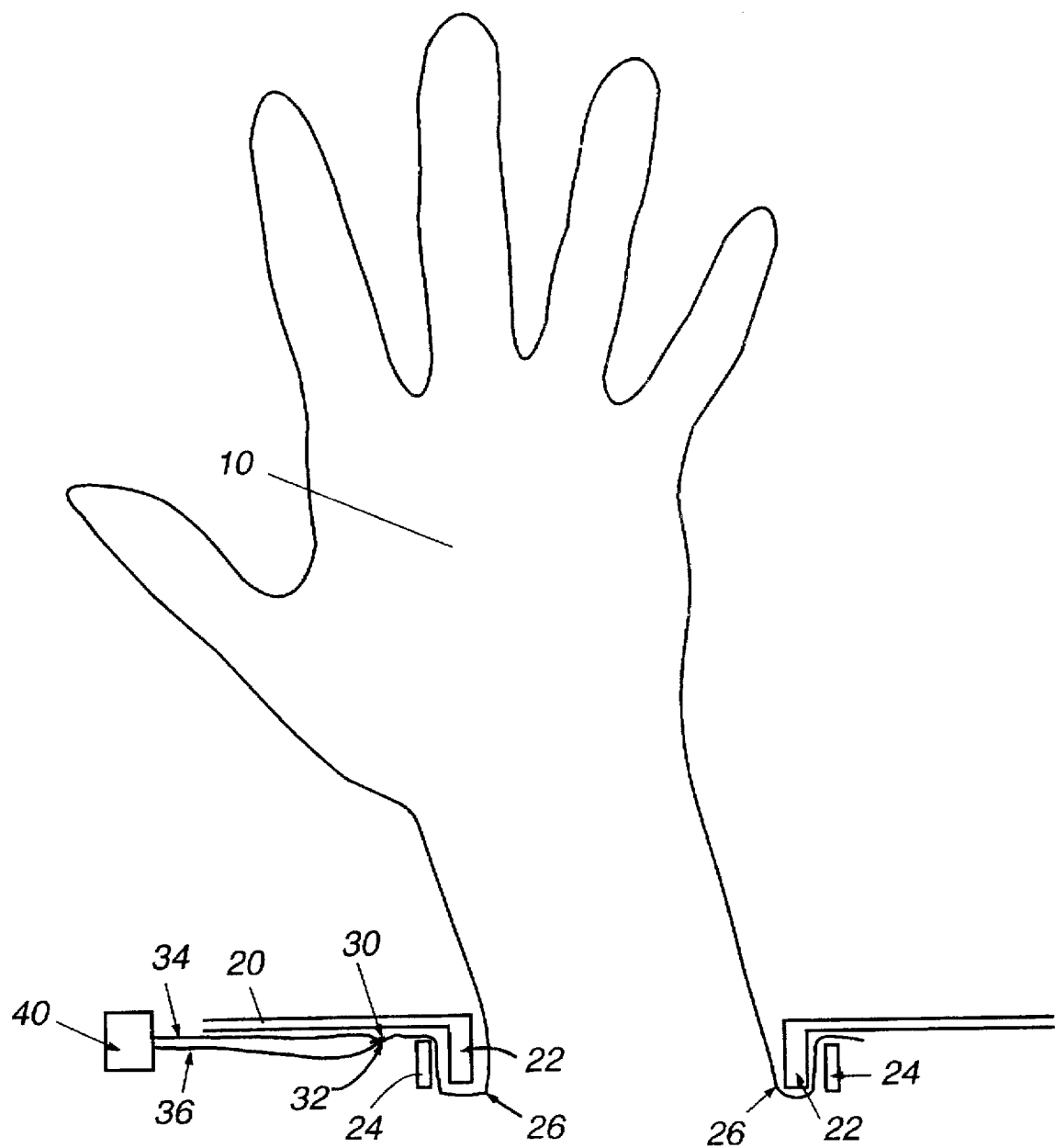
FIG. 1 is a plan view of a glove of the type used in glove boxes, manufactured in accordance with the present invention.

There has been discovered a method of monitoring the integrity of a protective barrier material by measuring the electrical resistance, conductivity or capacitance across two electrically conductive layers separated by an electrically insulative layer in a specifically designed multilayer protective barrier material. When the appropriate materials are used for the layers, then any puncture, cut or tear through the layers, regardless of size or characteristics, will result in contact between the two electrically conductive layers. This contact will cause changes in the electrical resistance, conductivity or capacitance transmitted by leads from the electrically conductive layers—changes which can be measured, monitored, used to signal an operator, or recorded.

The nonconducting barrier layer or layers can be made of any flexible rubber or elastomeric material which does not conduct electrical current. Choice of material will depend upon the desired properties suitable for the application in which the material is to be used, the selection of conductive materials to be used, and other considerations such as economic feasibility. Examples of useful nonconducting barrier layer materials include, but are not limited to: polyethylene (available from DuPont as Tyvek™, Phillips Petroleum as Marlex™); modified polyethylenes including chlorosulfonated polyethylene (available from DuPont as Hypalon™) and other functionalized polyethylenes; polyethylene copolymers including polyethylene-vinyl alcohol, poly(ethylene-propylenediene) and other copolymers; functionalized polyethylene copolymers including sulfonated poly(ethylene-propylene-diene) and others; poly(vinyl chloride) and copolymers of poly(vinyl chloride); poly (vinylidene chloride) (available as Saran™ from Dow Chemical); natural rubbers such as poly(trans-isoprene) (Balata and Gutta-percha) and poly(cis-1,4-isoprene) (Hevea and Guayule); synthetic rubbers including poly(cis-1,4-isoprene) and poly(isobutylene); functionalized synthetic rubbers including poly(ethylene-sulfide) (available as polysulfide rubber from Morton Thiokol); poly(trans-2-chloro-1,3-butadiene) also known as poly(chloroprene) (available from Ansell-Edmont as Neoprene™); synthetic rubber copolymers including poly(acrylonitrile-butadiene), poly(styrene-butadiene) and poly(styrene-isoprene); poly (dimethylsiloxane) (available as silicone rubber from Dow Chemical); and other elastomers including all types of poly(urethanes) and poly(acrylic esters).

Materials which can be used for the conducting layers of the invention materials can be either: (a) polyelectrolytes (ionic compounds and their salts); or (b) unsaturated polymers that have been "doped" to impart electrically conductive properties; or (c) polymers which have been modified with finely divided powders which impart conductivity to the material or enhance conductivity of the material; or (d) combinations thereof.

Examples of polyelectrolytes which are useful in the invention include, but are not limited to: poly(acrylic acid) and copolymers thereof; poly(vinyl acetate), and hydrolyzed poly(vinyl acetate); poly(vinyl alcohol-blend-metaphosphoric acid); poly(vinyl alcohol) with phosphoric acid; poly(ethylene sulfonic acid), i.e., polyvinylsulfonic acid; poly(acrylaminomethyl propane sulfonic acid), i.e., AMPS; poly(ethyleneimine); poly(2-oxazoline)s and hydrolyzed poly(2-oxazoline)s; poly(ethylene oxide), i.e., PEO; poly(propylene oxide), i.e., PPO; poly(methoxyethoxyethoxyphosphazene), i.e., MEEP; poly(galactomamaan), i.e., Guar gum, and derivatives thereof; poly(glucose-g-glucuron-co-mannose), i.e., Xanthan gum; and poly(acetamidodeoxyglucan), i.e., Chitin or Chitosan, and derivatives thereof. Useful salts include Li, Na, K, etc., as salts of poly(acrylic acid) and copolymers thereof, poly (ethylene sulfonic acid), poly(acrylaminomethyl propane sulfonic acid); various lithium salts compounded with poly (ethylene oxide), poly(propylene oxide) and poly (methoxyethoxyethoxyphosphazene); and NaCl, LiCl, LiOH, $K_2SO_4$, $K_3PO_4H_2O$ or most aqueous electrolyte salts compounded with poly(vinyl acetate), hydrolyzed poly (vinyl acetate), poly(vinyl alcohol-blend-metaphosphoric acid), poly(vinyl alcohol) with phosphoric acid, poly (ethyleneimine), poly(2-oxazoline)s, hydrolyzed poly(2-oxazoline)s, poly(galactomannan), poly(galactomannan) derivatives, poly(glucose-g-glucuron-co-mannose), poly (acetamidodeoxyglucan), and poly(acetamidodeoxyglucan) derivatives.

Examples of electrically conductive polymers which are useful in this invention include, but are not limited to:

poly(acetylene), poly(acetylene) derivatives, poly(pyrrole), poly(pyrrole) derivatives, poly(thiophene), poly(thiophene) derivatives, poly(phenylene), poly(phenylene) derivatives, poly(phenylenesulfide), poly(phenylenesulfide) derivatives, poly(phenylenevinylene), poly(phenylenevinylene) derivatives, poly(thienylenevinylene), poly(thienylenevinylene) derivatives, poly(aniline), and poly(aniline) derivatives. For dopants, $I_2$, $Br_2$, Li, Na, and $AsF_5$ salts can be used to enhance conductivity of poly(acetylene) and poly(acetylene) derivatives; $BF_4^-$, $ClO_4^-$ and tosylate salts can be used to enhance conductivity of poly(pyrrole), poly(pyrrole) derivatives, poly(thiophene) and poly(thiophene) derivatives; $AsF_5$, Li and K salts can be used to enhance conductivity of poly(phenylene) and poly(phenylene) derivatives; $AsF_5$ salts can be used to enhance conductivity of poly(phenylenesulfide), poly(phenylenesulfide) derivatives, poly(phenylenevinylene), poly(phenylenevinylene) derivatives, poly(thienylenevinylene) and poly(thienylenevinylene) derivates; inorganic and organic acids, polyacids and the like can be used to enhance conductivity of poly(aniline) and poly(aniline) derivatives.

Examples of substances which can be employed to impart conductivity or enhance conductivity of polymers used in the conducting layers of the invention materials include, but are not limited to, amorphous carbon (carbon black), crystalline carbon (graphite), silver, copper, zinc, aluminum, iron, tin, and combinations thereof. Presently preferred for many of the polymers which can be used in this invention is carbon. Generally these substances are incorporated in the polymers in the form of finely divided powders.

Any of the selected polyelectrolytes and conducting polymers must be of a consistency such that any instrument which punctures, breaks or tears the protective barrier material will cause at least one of the conductive layers to pull through the nonconductive layer and make contact with another conductive layers. Therefore, the selected conductive polymer material may need to be slightly plasticized in order to be effective at making a "pull-through" contact between the at least two electrically conductive layers. Examples of compounds useful for plasticizing polyelectrolytes include, but are not limited to, glycerol (also called glycerine), aliphatic organic acids and esters, and various high boiling solvents such as dimethyl formamide, N-methyl pyrrolidone, dimethylsulfoxide, and the like. Dimethyl formamide, N-methyl pyrrolidone, dimethylsulfoxide and other high boiling solvents are also among the compounds useful for plasticizing conducting polymers which can be used in this invention.

In a presently preferred embodiment useful for glove box gloves, the conductive layers are formed of poly(vinyl alcohol) containing approximately 0.5 to 70% by weight glycerol and from about 0.5 to about 20% by weight of a salt such as sodium chloride. Use of too little salt will not provide the desired conductivity. Use of too high a concentration of salt could result in crystallization of the salt which causes total loss of conductivity. The glycerol functions as a softening agent to give the poly(vinyl alcohol) properties that permit it to be drawn through the insulating layer upon puncture, thereby closing an electrical circuit between the two conductive layers.

In this preferred embodiment for use in glove box gloves, the nonconductive insulating inner layer is formed of poly(trans-2-chloro-1,3-butadiene), commonly known as poly(chloroprene). When the glove box gloves are to be used as protection against radioactivity, the insulating inner layer of poly(chloroprene) is loaded with approximately 70 to 90% by weight (or 10 to 30% by weight of the total glove material) finely divided red lead oxide particles to serve as a barrier to radiation from radioactive materials. Other common radiation barriers and their oxides may also be used.

The exterior layers of this preferred embodiment are formed of an elastomeric chlorosulfonated polyethylene having good chemical resistance, particularly to acidic environments.

The invention material can be made in any of the ways known in the art for manufacturing multilayer polymeric materials. Polymeric material in solution can be laid down in layers, then after each layer is dried, each subsequent layer can be applied the same way. One adaptation of this method is that used for making polymer gloves: a mandrel in the shape of a hand can be dipped sequentially into solutions of the polymers, letting each layer of polymer dry or cure before dipping the mandrel into the polymer solution for the next layer. Each layer can be air dried or oven dried for quicker drying and curing (see, e.g., U.S. Pat. No. 3,025,403, incorporated herein by reference).

Alternatively, for sheets of the multilayered protective barrier material, the polymers can be extruded. Each layer can be separately extruded with the layers being combined after extrusion by thermal, pressure, chemical adhesive or solvent means or combinations of these means of combination of the layers. Another way of producing the multilayered protective barrier material in sheets is by co-extrusion of the layers as thin films.

The electrically conductive contacts may be: (a) simply implanted portions of the electrical leads away from the conductive layers; (b) portions of electrically conductive material or electrode contacts specifically configured to attach to the electrically conductive leads and to the conductive layers by means of tiny hooks, electrically conductive cement, or simply implanted in the conductive layers; or (c) extensions of the conductive layers.

The electrode contacts could be metallic inserts such as wires, meshes, pins, films, patterned films, woven wires, or any other thin electrode material design which provides sufficient contact between the electrode lead and the conductive layers.

Because of the often corrosive effects of the ionic salts in the conductive layers, the lead wires and/or electrode contacts generally are composed of non-corrosive metals such as stainless steel, silver, titanium, zirconium, niobium, tantalum, hafnium, platinum, zinc, noble metals such as gold, and the like; or alloys such as, for example, cupronickel, cuprotin, cuprozinc, alloys of chrome and nickel; or plated alloys or metals such as zinc plated copper. Wires such as thermocouple wires or similar materials can be used for the leads.

The measuring of the resistance, conductivity or capacitance can be performed by any appropriate means such as by use of a simple multimeter (voltmeter), continuity tester, or an inexpensive, battery-powered "black box" that will alarm when the glove resistance is reduced to some preset value. For example, the resistance measuring means could be a low power ohm meter set to sound an alarm, move an indicator, or respond in some planned way whenever megaohms in a certain range are sensed. Thus a puncture can be detected at the time the puncture occurs, enabling a user to be alerted and to take appropriate measures in a timely manner. The device measuring the electrical resistance can send out a warning signal or mark an indicating device such that any contact between the conductive layers, no matter how brief in time, would be detectable by a person operating the monitoring system. FIG. 1 illustrates a preferred embodiment of the invention because lead-loaded gloves used during the processing of nuclear materials are a common barrier application for which the invention materials would be particularly appropriate. FIG. 1 shows a glove 10 attached to a wall 20 of a glove box by having the cuff portion of the glove 26 rolled over a projection 22 on the glove box wall and secured by a ring clamp 24.

Figure 2:
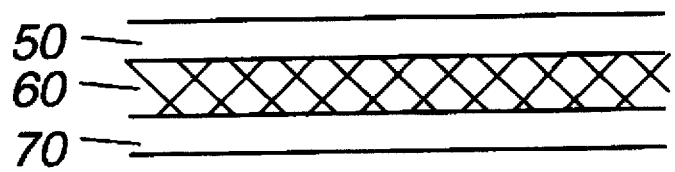
FIG. 2 is a cross section of a material currently used to manufacture gloves for use in glove boxes.

With reference to FIG. 2, the commonly used glove box gloves are made from flexible polymeric material having at least three layers: an outer layer 50 formed of a chemically resistant material such as a chlorosulfonated polyethylene polymer; an enclosed layer 60 formed of a radioactive barrier material such as lead loaded polychloroprene; a second exterior layer 70 (which would be the inner layer of the formed glove) of a chemically resistant material such as a chlorosulfonated polyethylene polymer which is usually the same as the outer layer 50. The exterior layers 50 and 70 generally have thicknesses in the range from about 0.001 to about 0.1 inch, with the exterior layer 50 on the outside of the glove being thicker than the exterior layer 70 on the inside of the glove. The enclosed lead loaded layer 60 is generally from about 0.001 to about 0.10 inch thick. An example of the manufacture of glove box gloves such as these is described in U.S. Pat. No. 3,025,403, incorporated herein by reference.

Figure 3:
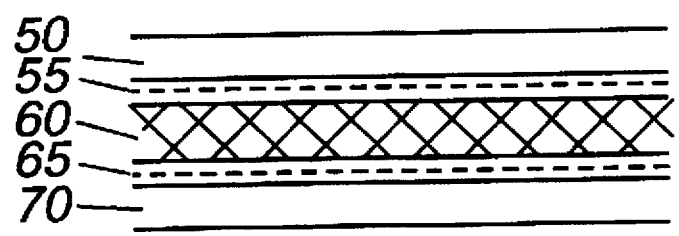
FIG. 3 is a cross section of the protective barrier material used in the invention gloves of FIG. 1.

With reference to FIG. 3, the invention material has an additional two layers 55 and 65, one of which 55 is immediately adjacent to the outer layer 50 and the enclosed layer 60 and the other of which 65 is immediately adjacent the inner layer 70 and the enclosed layer 60. The two additional layers 55 and 65 are formed of electrically conductive material such as, for example, poly(vinyl alcohol) containing from about 0.5 to about 70 percent by weight glycerol and approximately from about 0.5 to about 20 percent by weight of an ionic salt such as sodium chloride. Each of the conductive layers 55 and 65 is from about 0.0001 to about 0.01 inch thick, thin enough to make no ordinarily perceptible addition to the total thickness of the glove material.

The glycerol is present in the conductive layers for the purpose of softening the conductive material so that the two layers of conductive material can make contact when a puncture, cut or tear occurs. The ionic salt is present for the purpose of imparting conductive electrical properties to the polymeric material.

With reference to FIGS. 1 and 3, electrical leads 34 and 36 are attached to each of the electrically conductive layers 55 and 65, respectively, by means of electrically conductive contacts 30 and 32. The electrically conductive contacts 30 and 32 may be simply portions of the electrical leads 34 and 36 implanted in the conductive layers 55 and 65; or the contacts 30 and 32 may be portions of electrically conductive material specifically configured to attach to the electrically conductive leads 34 and 36 and to the conductive layers 55 and 65 by means of tiny hooks, electrically conductive cement, or simply by being implanted in the conductive layers as the conductive layers are being formed or by insertion after the conductive layers are formed.

Still with reference to FIGS. 1 and 3, the conductive layers 55 and 65 are connected by means of the electrical contacts 30 and 32 and electrical leads 34 and 36 to a suitable apparatus 40 for measuring the electrical resistance, conductivity, or capacitance between the layers 55 and 65. Because of the insulative properties of the enclosed layer 60 which is made of nonconductive material and the insulative properties of the nonconductive inner and outer layers 50 and 70, the electrical resistance measured between layers 55 and 65 is virtually infinite when there are no punctures or completed electrical pathway allowing contact between the conductive layers 55 and 65.

The formulation of the layers 55 and 65 is such that they are sufficiently elastic or tacky to deform and stretch during puncturing of the glove 10. The deformation and stretching of the punctured conductive layer 55 through the nonconductive enclosed insulative layer 60 results in contact between layers 55 and 65. The contact between layers 55 and 65 will cause a measurable decrease in electrical resistance.

Alternatively, depending upon the materials to be handled with the glove, an electrically conductive material having sufficient elasticity and tackiness to function as either of the electrically conductive layers 55 and 65 can be used in place of the outer layer 50 or inner layer 70, respectively, thus eliminating the need for one or both of the additional electrically conductive layers 55 and 65. The electrically conductive layers 50 and 70 would still be separated by the nonconducting layer 60, resulting in virtually infinite resistivity until there were some contact between the conductive layers 50 and 70 indicative of some breach in the integrity of the layers somewhere in the glove.

The measuring of the resistance, conductivity or capacitance can be performed by any appropriate means such as by use of a simple multimeter (voltmeter) 40, continuity tester 40, or an inexpensive, battery-powered "black box" 40, that will alarm when the glove resistance is reduced to some preset value. For example, the resistance measuring means 40 could be a low power ohmmeter set to sound an alarm, move an indicator, or respond in some planned way whenever a resistance less than infinite ohms occurs or when a chosen conductivity of the conductive layers 55 and 65 occurs. The chosen conductivity will depend upon the materials used.

Use of this type of monitoring method with glove box gloves, and indeed with other types of protective clothing, permits freedom of movement and does not hinder or limit a worker while continuous monitoring is being accomplished. There is no necessity for having leads attached to the worker's person, as is the case with most of the medical glove monitoring systems.

The materials of this invention can be used to help ensure the safety of personnel who handle and dispose of hazardous and radioactive materials by providing a means for continuous real-time monitoring of the integrity of the protective barrier the material forms. Decontamination costs associated with punctures, cuts or tears in protective barriers are minimized by real-time detection of breaches of the integrity of the protective barrier material. For example, real-time detection of punctures, cuts or tears enables the user to take appropriate measurements to inspect for contamination before there has been a significant opportunity for dissemination of the radioactive contaminants.

EXAMPLE I

Figure 4:
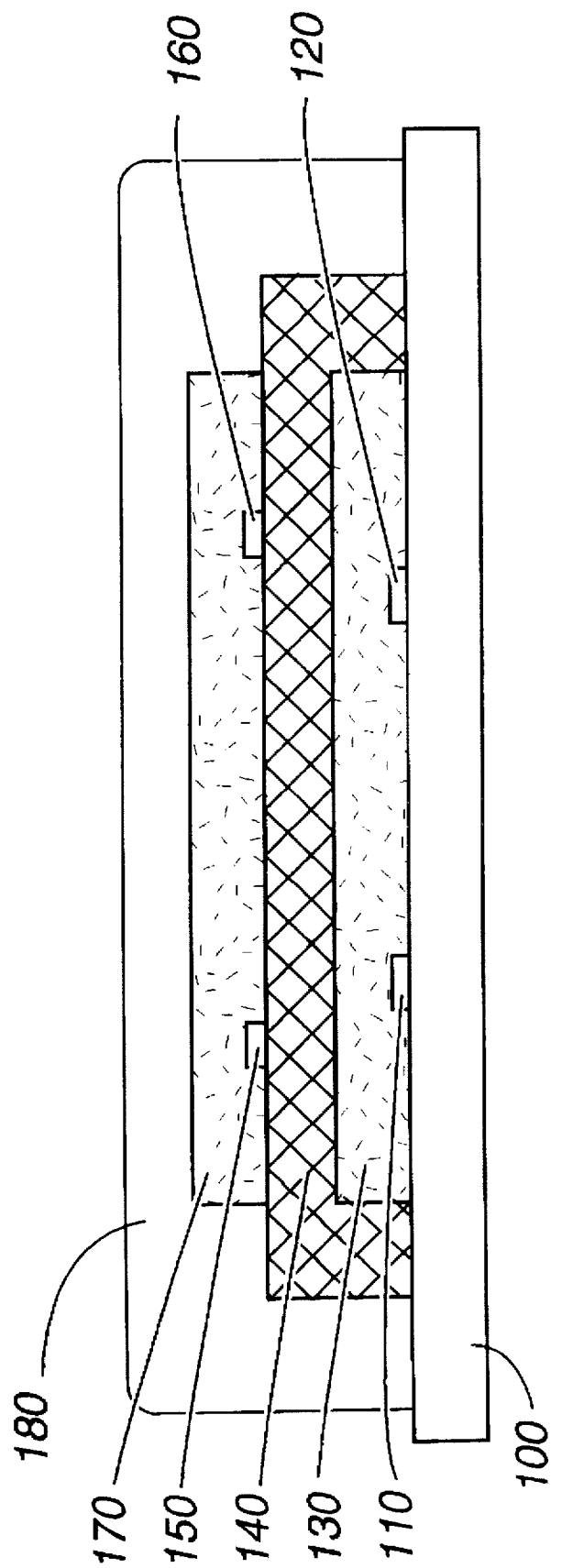
FIG. 4 is a cross section of test patches of protective barrier material of the invention.

To demonstrate operability of the invention, a circular test patch of invention material was fabricated and subjected to a puncture. The test patch was designed to approximate the commercially available multilayer material used for glove box gloves which attenuate radiation with the exception that two additional electrically conductive layers were added. A schematic of the cross section of the test patch is shown in FIG. 4. A commercially available glove used for comparative purposes was obtained from North Hand Protection, 4090 Azalea Drive, Charleston, S.C. 29415. The comparative glove had three layers: 0.010" thick Hypalon™ (chlorosulfonated polyethylene); 0.015" thick lead-loaded Neoprene™ (polychloroprene); and 0.005" Hypalon™ for a total thickness of 0.030 inches. FIG. 2 shows a cross section of the comparative glove material. The comparative glove was made by successively dip-coating then oven drying a hand-shaped mandrel in a solution of the suspended solids of each of the layer materials.

For preparing the test patch, samples of the same dip-coat solution materials used in manufacture of the comparative glove were obtained from the manufacturer of the comparative glove. The Hypalon™ and Neoprene™ samples were synthetic rubbers with additives in a 50/50 solvent mixture of toluene/xylene. The Hypalon™ had about 18.5% by weight suspended solids (i.e., polymer/solvent) as tested by comparing the weight of a sample before and after solvent removal. The Neoprene had about 37% solids which consisted of about 7.4% polymer and 29.6% finely divided red lead oxide ($Pb_3O_4$) particles. These were measured in the same manner as the Hypalon™ solids.

For use as the electrically conductive layers in the test patch, a polyelectrolyte was prepared from an aqueous solution containing 2% NaCl, 4% glycerol, and 5% poly (vinyl alcohol), on a weight to volume basis. The salt was the electrolyte which allowed electrical conductivity. The glycerol was the plasticizer for the poly(vinyl alcohol) based polymer.

A schematic of the cross section of a test patch is shown in FIG. 4; the actual test patch had depositional layers which were not as "squared off" at the circumferences of the layers. The thicknesses of the layers is not shown to scale in the figure. The test patch, shown in FIG. 4, was prepared by first depositing a 2.8-inch diameter, 0.010-inch thick circular film of Hypalon™ on a flat glass substrate. The first Hypalon™ layer 100 was air dried overnight. Then two 3.0" electrical leads of 0.013" diameter Chromel-P™ wire were placed on top of the surface of the first Hypalon™ layer 100 with horizontal separation of 1.4". See leads 110 and 120 in FIG. 4. The Chromel-P™ lead material (commercially available from Hoskins Manufacturing Company, Detroit, Mich.) was an alloy of 20% chrome and 80% nickel as is commonly used in thermocouple wire.

After placement of the two 3.0" electrical leads 110 and 120, a 2.0-inch diameter, 0.010-inch thick circular film of the polyelectrolyte 130 was deposited onto the center of the first Hypalon™ layer and air dried overnight. After drying of polyelectrolyte layer 130, a 2.4" diameter, 0.020-inch thick circular film 140 of the lead-loaded Neoprene™ was deposited in the center of the test patch and air dried overnight. A second set of 3" electrical leads with a 0.013" diameter (150 and 160 in FIG. 4) were placed on top of the surface of the lead-loaded Neoprene™ layer 140 with a separation of 1.4 inches.

After placement of the second set of electrical leads 150 and 160, a second 2.0-inch diameter, 0.015-inch thick layer of the polyelectrolyte layer 170 was deposited onto the center of the test patch and air dried overnight. A final 2.8-inch diameter, 0.005-inch thick Hypalon™ layer 180 was then deposited onto the center of the test patch and air dried overnight.

The five-layer test patch had a total thickness of 0.060-inch which was twice the total thickness of the three-layer comparative glove material. However, the test patch material was still very flexible as would be needed for glove box glove material.

The electrical conductivity of each of the polyelectrolyte layers in the test patch was tested by attaching an electrical multimeter (Fluke Model 77, digital display) to the opposing electrical leads embedded within each of the polyelectrolyte layers. The multimeter was set for resistance measurements. The electrical resistance across the first polyelectrolyte layer measured with leads 110 and 120 was 13 M-ohms. The electrical resistance across the second polyelectrolyte layer measured with leads 150 and 160 was 14 M-ohms. These measurements show that each of the polyelectrolyte layers were conducting electrical charges within each of the layers, as would be expected with the material chosen partly for its conductive properties.

The resistance between electrical leads 110 and 150, 120 and 160, 110 and 160, and between 120 and 150 was measured by connecting the electrical leads in pairs to the same multimeter. The resistance measured in each case was infinite, meaning that there was no measurable conductivity between the first polyelectrolyte layer 130 and the second polyelectrolyte layer 170.

A 0.047-inch diameter steel pin was pushed through the test patch while the resistance across leads 110 and 150 was monitored. The electrical resistance, which prior to the pin puncture had been infinite, immediately came on-scale with an average reading of 13 M-ohms. The pin was removed, and after 5 minutes the resistance gradually increased to a value of 30 M-ohms. The pin was pushed back into the same hole while the resistance was still being monitored. The resistance instantly decreased from 30 M-ohms to a value of 16 M-ohms, showing that there was an increase in conductivity between the two polyelectrolyte layers when the pin was reinserted.

EXAMPLE II

A second set of tests were made on test patches which had been aged for a period of 11 months. The same test patch which had been punctured with the pin in Example I was aged under ambient conditions by storage in a plastic bag in a file folder. Tests of conductivity of the second polyelectrolyte layer 170 and conductivity between each of the polyelectrolyte layers 130 and 170 (shown in FIG. 4) were made in the same manner as described in Example I. Resistance between the two electrical leads 150 and 160 on the second polyelectrolyte layer 170 was measured at a value of 28 M-ohms, which showed that the polyelectrolyte layer was still electrically conductive. Resistance between the conductive layers at electrical leads 110 and 160 was measured at 30 M-ohms. This shows that after 11 months there was still electrical conductance between the two polyelectrolyte layers indicative of the presence of the 11-month old puncture in the glove material.

EXAMPLE III

Another sample test patch was prepared as described in Example I, but was aged under ambient conditions in a plastic bag in a file folder for 11 months before being punctured or tested. The polyelectrolyte layers of this second test patch were tested in the same manner as those described in Example I using a multimeter connected to electrical leads imbedded in multilayer material as shown in FIG. 4. The resistance across the first polyelectrolyte layer 130 was 29 M-ohms and the resistance across the second polyelectrolyte layer 170 was 28 M-ohms, indicating that each of the polyelectrolyte layers was still conductive after 11 months. The resistance between the two polyelectrolyte layers was off-scale, indicating that there was no measurable conductivity between the two polyelectrolyte layers.

A 0.047" diameter steel pin was pushed through the aged test patch while the resistance between the two polyelectrolyte layers was monitored at leads 110 and 160. Resistance of 38 M-ohms was measured, indicating that there was electrical conductivity between the two polyelectrolyte layers 130 and 170 when the test patch had a puncture pin in place. A test of the resistivity between the two polyelectrolyte layers 130 and 170 using leads 110 and 150 gave a reading of 32 M-ohms. Removal of the pin resulted in resistance readings that went off scale (infinity), indicating that there was no longer conductivity between the two polyelectrolyte layers. This means that when the invention puncture detecting barrier materials are used a signal indicating a breach of the integrity of the barrier material may be discontinuous.

A further test of this same aged material was made to determine the effect of punctures or tears made with non-conductive materials. A pointed 0.085-inch diameter wooden dowel was used to puncture the sample test patch in a place offset from the place where the metal pin puncture was made. The resistance measurement immediately came on-scale with a reading of 35 M-ohms. This demonstrated that even when punctures were caused by nonconductive materials such as wood, the puncture detecting barrier material still worked as expected, i.e., a puncture caused physical contact between the two polyelectrolyte layers in a mechanical way so as to make a measurable electrical connection between the two which then triggered a monitoring device.

INDUSTRIAL APPLICABILITY

The protective barrier puncture detecting materials of this invention can be used for any application requiring the maintenance of integrity of a barrier between toxic, bioactive, radioactive and other hazardous materials and people and equipment with which people may come into contact. The protective barrier material and method of this invention are useful for containment bags, container liners, environmental liners, covers for hazardous storage containers, gaskets or seals and protective apparel such as gloves, aprons, boots, pants, smocks, face shields, gowns and the like.

The present invention is particularly suited to manufacture of gloves for use in glove boxes, and is even more particularly suited to gloves used for handling radioactive materials, where prompt detection of punctures, cuts or tears is desirable to avoid dispersal of radioactive contaminants.

That which is claimed is:

1. A multiplayer protective barrier material comprising:
   at least one internal layer of an electrically insulating flexible polymeric material;
   first and second electrically conductive layers of flexible polymeric material, said first and second electrically conductive layers being located on opposite sides of at least one of said at least one internal layer of electrically insulating material;
   with at least one of said first and second electrically conductive layers being of a consistency such that a puncture in said multilayer protective barrier material would cause said at least one electrically conductive layer to pull through said at least one internal layer of electrically insulating material; and
   a means for measuring conductivity connected to each of said first and said second electrically conductive layers.

2. A glove made of the material recited in claim 1.

3. A multilayer protective barrier material as recited in claim 1, wherein said electrically conductive layers have therein at least one substance chosen from the group of carbon, silver, copper, zinc, aluminum, iron, tin, and combinations thereof.

4. A multilayer protective barrier material as recited in claim 3, wherein said electrically conductive layers have therein carbon.

5. A multilayer protective barrier material as recited in claim 1, wherein said at least one internal layer of electrically insulating material comprises polychloroprene, and said electrically conductive layers comprise poly(vinyl alcohol).

6. A multilayer protective barrier material as recited in claim 1, wherein said at least one internal layer of electrically insulating material comprises a barrier to radioactivity.

7. A multilayer protective barrier material as recited in claim 1 wherein said first and second electrically conductive layers are external layers.

8. A multilayer protective barrier material as recited in claim 1 having at least one additional layer external to at least one of said first and said second electrically conductive layers.

9. A multilayer protective barrier material as recited in claim 8 wherein said at least one additional layer is comprised of chlorosulfonated polyethylene.

10. A multiplayer protective barrier material comprising:
    at least one internal layer of an electrically insulating material;
    first and second electrically conductive layers, said first and second electrically conductive layers being located on opposite sides of at least one of said at least one internal layer of electrically insulating material;
    wherein said electrically conductive layers have therein at least one electrolyte salt; and
    a means for measuring conductivity connected to each of said first and said second electrically conductive layers.

11. A multilayer protective barrier material as recited in claim 10, wherein said electrically conductive layers have therein sodium chloride.

12. A method for detecting breaches of the integrity of a protective barrier material comprising: (a) measuring the electrical conductivity between two electrically conductive layers separated by an electrically insulative layer in said barrier material wherein at least one of said two electrically conductive layers is of a consistency such that a puncture in said protective barrier material would cause said at least one electrically conductive layer to pull through said electrically insulative layer; and (b) comparing electrical conductivity between said two electrically conductive layers with normal conductivity across said electrically insulative layer.

13. A method for detecting breaches of the integrity of a protective barrier material comprising: (a) measuring the electrical resistance between two electrically conductive layers separated by an electrically insulative layer in said barrier material wherein at least one of said two electrically conductive layers is of a consistency such that a puncture in said protective barrier material would cause said at least one electrically conductive layer to pull through said electrically insulative layer; and (b) comparing electrical resistance between said two electrically conductive layers with normal electrical resistance across said electrically insulative layer.

14. A method for detecting breaches in the integrity of a protective barrier material comprising: (a) measuring the electrical capacitance between two electrically conductive layers separated by an electrically insulative layer in said barrier material wherein at least one of said two electrically conductive layers is of a consistency such that a puncture in said protective barrier material would cause said at least one electrically conductive layer to pull through said electrically insulative layer; and (b) comparing electrical capacitance between said two electrically conductive layers with normal electrical capacitance across said electrically insulative layer.

* * * * *